US012769988B2

(12) United States Patent
Eidam et al.

(10) Patent No.: US 12,769,988 B2
(45) Date of Patent: Oct. 20, 2026

(54) GENERATIVE ADVERSARIAL NETWORK RECOMMENDATION ENGINE

(71) Applicant: Wells Fargo Bank, N.A., San Francisco, CA (US)

(72) Inventors: Kourtney Eidam, Marietta, GA (US); Senthil Soundararajan, San Ramon, CA (US); Dana S. Stevenson, San Francisco, CA (US)

(73) Assignee: Wells Fargo Bank, N.A., San Francisco, CA (US)

( * ) Notice: Subject to any disclaimer, the term of this patent is extended or adjusted under 35 U.S.C. 154(b) by 107 days.

(21) Appl. No.: 18/673,658

(22) Filed: May 24, 2024

(65) Prior Publication Data

US 2025/0363336 A1 Nov. 27, 2025

(51) Int. Cl.

| | |
|---|---|
| ***G06N 3/0475*** | (2023.01) |
| ***G06Q 30/0601*** | (2023.01) |
| ***G16H 50/30*** | (2018.01) |
| *G06F 21/62* | (2013.01) |

(52) U.S. Cl.

CPC ....... *G06N 3/0475* (2023.01); *G06Q 30/0631* (2013.01); *G16H 50/30* (2018.01); *G06F 21/6254* (2013.01)

(58) Field of Classification Search

CPC ........... G06Q 40/0821; G06Q 30/0631; G06N 3/0475; G16H 50/30; G06F 21/6254

See application file for complete search history.

(56) References Cited

U.S. PATENT DOCUMENTS

| | | | |
|---|---|---|---|
| 10,325,070 | B2 | 6/2019 | Beale et al. |
| 10,664,572 | B2 | 5/2020 | Bitran et al. |
| 10,878,479 | B2 | 12/2020 | Wu et al. |
| 11,501,042 | B2 | 11/2022 | Steingrimsson et al. |

(Continued)

FOREIGN PATENT DOCUMENTS

| | | | |
|---|---|---|---|
| CN | 115470705 | | 12/2022 |
| KR | 20230080939 | A * | 6/2023 |
| WO | 2021159776 | | 8/2021 |

OTHER PUBLICATIONS

Akash Takyar “Generative AI in insurance_ A comprehensive guide” Available online Aug. 16, 2023 << https://web.archive.org/web/20230816181528/https://www.leewayhertz.com/generative-ai-in-insurance/>> retrieved on Oct. 18, 2025.*

(Continued)

*Primary Examiner* — Peter H Choi

(74) *Attorney, Agent, or Firm* — SCHWEGMAN LUNDBERG & WOESSNER, P.A.

(57) ABSTRACT

Systems and techniques for are described herein. Profile data is obtained for a user and an organization and preprocessed to generate a normalized data set. A generative adversarial network is trained using features extracted from the normalized data set. A set of synthetic profiles are generated using the generative adversarial network. A set of healthcare plan recommendations are derived using the set of synthetic profiles. Justification context is determined for each healthcare plan recommendation. An interactive healthcare plan recommendation user interface is generated comprising the set of healthcare plan recommendations and the justification context for output on a display device.

14 Claims, 5 Drawing Sheets

(56) References Cited

U.S. PATENT DOCUMENTS

| | | | | |
|---|---|---|---|---|
| 2016/0378932 | A1 * | 12/2016 | Sperling ................ | G06Q 40/08 705/3 |
| 2017/0091838 | A1 | 3/2017 | Cunico et al. | |
| 2017/0308800 | A1 | 10/2017 | Cichon et al. | |

OTHER PUBLICATIONS

Min Gao et al. "Recommender systems based on generative adversarial networks: A problem-driven perspective" 2020.*

* cited by examiner

GENERATIVE ADVERSARIAL NETWORK RECOMMENDATION ENGINE

TECHNICAL FIELD

Embodiments described herein generally relate to generative adversarial network training and, in some embodiments, more specifically to training a generative adversarial network recommendation engine.

BACKGROUND

Selecting a healthcare plan is a complex decision-making process that involves considering numerous variables, including costs, benefits, employee demographics, health conditions, and regulatory compliance. Small businesses, in particular, face challenges due to limited resources and expertise in evaluating and choosing the most appropriate healthcare plans for their employees. Traditional methods of selecting healthcare plans often involve manual research and comparison, which can be time-consuming and may not result in the most cost-effective or beneficial outcomes.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Existing tools and services that aim to assist in generating healthcare plan recommendations are limited in their ability to provide personalized recommendations. They may not take into account the unique characteristics of each business or the individual health profiles of employees. Furthermore, these tools may not be equipped to adapt to the changing regulatory landscape or to incorporate feedback from users to improve the quality of recommendations over time.

The systems and techniques discussed herein provide an improved system and method that leverages advanced artificial intelligence (AI) techniques to provide comprehensive, personalized, and adaptive recommendations for healthcare plans. A wide range of data inputs are processed, including but not limited to, local laws, business size, employee demographics, health spending history, and feedback from similar entities. Additionally, privacy concerns are respected by ensuring that sensitive employee health data is used in a manner that is compliant with applicable regulations and that employees have control over their data through opt-in mechanisms.

The AI-based recommendation system utilizes a generative adversarial network (GAN) to analyze various data points and generate healthcare plan recommendations for small businesses (and other organizations) and their employees. The system is designed to consider a multitude of factors, including local regulations, business requirements, employee health profiles, and financial transactions, to provide a tailored set of healthcare plan options.

The AI model is trained using historical data and feedback to refine the recommendations and improve accuracy over time. Justifications are provided for each recommendation, thereby offering transparency into the decision-making process.

A privacy-centric approach is used where data is collected and used with the consent of the businesses and employees, ensuring compliance with privacy laws and regulations. The system is designed to be flexible and adaptable to various regulatory environments, making it suitable for small businesses in different jurisdictions.

The technical aspects of the invention, including data integration, model training, algorithmic decision-making, and system implementation, are designed to provide an efficient and user-friendly solution for healthcare plan selection, ultimately leading to better health outcomes and cost savings for small businesses and their employees.

Figure 1:
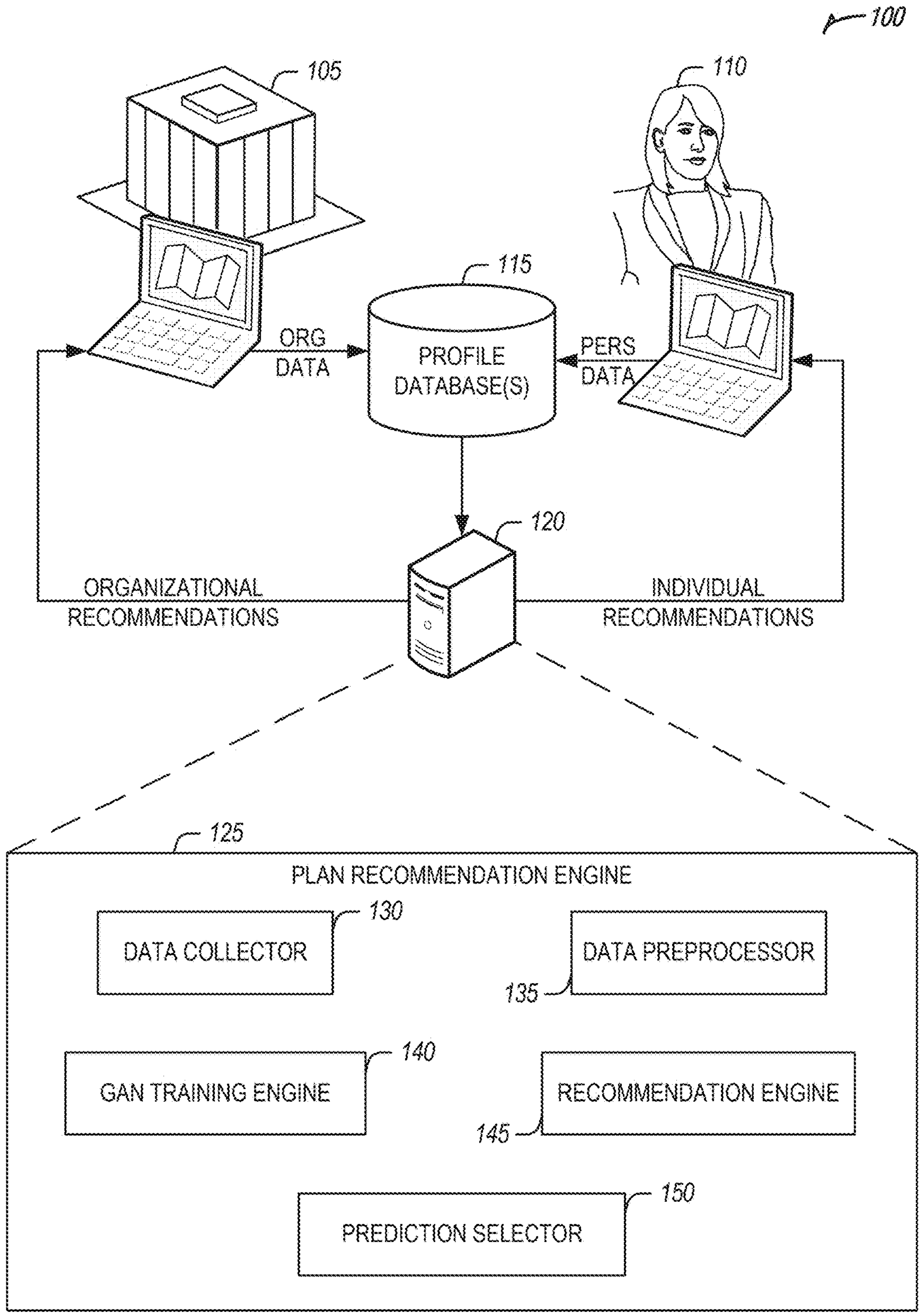
FIG. 1 is a block diagram of an example of an environment and a system for a, according to an embodiment.

FIG. 1 is a block diagram of an example of an environment 100 and a system 125 for, according to an embodiment. The environment 100 may include a computing device (e.g., a smartphone, tablet, laptop computing device, desktop computing device, etc.) for an organization 105, a computing device for a user 110, a profile database 115, a server computing device 120 (e.g., a standalone server, a cloud computing platform, a virtualized computing device, a field programmable gate array (FPGA), an application specific integrated circuit (ASIC), a system on chip (SoC), etc.). The server computing device 120 may include the system 125. In an example, the system may be a plan recommendation engine. The system 125 may include a variety of components including a data collector 130, a data preprocessor 136, a generative adversarial network (GAN) training engine 140, a recommendation engine 145, and a prediction selector 150.

The computing device of a user 110 and a computing device of an organization 105 may submit data to a profile database 115. It should be understood that the profile database 115 may include one database or a collection of databases. The data may be submitted directly to the profile database 115 or may be collected from user data based on data sharing privileges assigned by the user defining privacy controls. The privacy controls may provide rules regarding types and locations of data that may be collected.

The data collector 130 and the data preprocessor 135 prepare data obtained from the profile database 115 for feature extraction. The data is cleaned, formatted, and privacy filters are applied before features are extracted from the data to be transmitted to the GAN training engine 140. The GAN training engine 140 trains a model that calculates predictions for suitability of a healthcare plan for the organization 105 as a whole and for the user 110 individually based on attributes of the organization 105 and the user 110. The recommendations are based on business size, local regulations, needs, predicted growth. Data used to train the models and make predictions includes health insurance plan data for plans used by similarly situated organizations within the state or local area, satisfaction ratings for those health insurance plans, local regulation data applicable to the organization 105, local law data for the organization 105, etc. In an example, an interface may be used to enable connections to multiple heath care plan providers to collect health plan data to facilitate authentication including a secure connection while providing interoperability to easily establish connections to additional health plan providers with applications, web requests, etc.

Data (e.g., behavioral data, transactional data, usage data etc.) for individual employees is collected and evaluated to extract features that are used to enable the GAN training engine 140 to calculate predictions that are used by the recommendation engine 145 and the prediction selector 150 to generate customized recommendations at varying levels of granularity. For example, a digital multimedia report may be generated and transmitted to the computing device of the organization 105 or the computing device of the user 110 that includes suggested health insurance plans and reasons why the plans were selected. The reasons may be displayed in a number of forms including by way of example and not limitation, lists of pros and cons, a bullet list, a natural language sentence or paragraph that explains user or organization attributes used to make the prediction and attributes of the plan that match the organization or user attribute, a tabular infographic, a grid with organization or user attributes on a first axis and health plan attribute on a second access, and the like.

The GAN training engine 140 architecture and training process enable personalization of healthcare plan recommendations while maintaining privacy through several key mechanisms. The GAN training engine 140 creates synthetic data that mimics the statistical properties of real-world data without exposing individual personal health information (PHI). This synthetic data is used to train the models without risking the privacy of the individuals whose data contributed to the model.

During the training process, techniques such as differential privacy may be applied to ensure that the synthetic data does not reveal sensitive information about the individuals in the training dataset. Differential privacy introduces controlled noise to the data or the model parameters, making it difficult to infer specifics about any individual.

Federated learning is a decentralized approach to training AI models where the model is trained across multiple devices or servers holding local data samples, without exchanging them. The models may be trained on a dataset of the organization 105 locally, and only model updates (and not the data itself) would be shared with a central server for aggregation. This preserves the privacy of respective organizations and users.

Homomorphic encryption allows computations to be performed on encrypted data without needing to decrypt it first. Models may be trained on encrypted data, ensuring that sensitive information remains secure throughout the process. The model learns from the encrypted data, and the resulting recommendations are also encrypted and are only accessible by authorized parties.

Secure multi-party computation (SMPC) enables parties to jointly compute a function over their inputs while keeping those inputs private. The models may be trained using SMPC to ensure that the data from different organizations and users is used in a way that preserves privacy while still benefiting from a diverse dataset.

Once the model is trained, it may generate personalized healthcare plan recommendations by inputting anonymized or pseudonymized data from individual users or organizations. Learned patterns from the synthetic data are used to predict the best plans for these anonymized profiles, ensuring that personalization does not compromise privacy.

The GAN training engine 140 may continue to learn from new data and feedback while maintaining privacy. As it receives more information about the effectiveness of the recommendations, it can adjust and improve without needing to access sensitive information directly.

By incorporating these privacy-preserving techniques into the GAN training engine 140 architecture and training process, personalized healthcare plan recommendations are generated that are tailored to the specific needs of organizations and their employees, without compromising the privacy and security of their data.

A recommendation generated by the recommendation engine 145 and the prediction selector 150 for the organization 105 may be considered a macro view of the recommended plans because the underlying data of the organization 105 and the user 110 is used to predict plans that meet the aggregate attributes of the organization 105 and the user 110 and select plans with the highest predictor value (e.g., 90% match over 30% match, etc.) for selection for presentation in a user interface. For example, a plan portfolio included int eh recommendation may include a variety of individual plans that will be available to the user 110 and match the user 110 attributes and the organization 105 attributes. The recommendation output includes plans that meet local laws and regulations applicable to the organization 105 and provide the highest predicted matches for the user 110 attributes and goals of the organization 105. For example, plans may be sorted using cost or overhead, benefit options, plan features (e.g., gym membership reimbursement, telehealth access, no-charge preventative visits, etc.), deductibles, perks, experience ratings, etc.

A recommendation generated by the recommendation engine 145 and the prediction selector 150 for the user 110 may be considered a micro view of the recommended plans because the underlying data of the user 110 is used to predict plans that meet the individual attributes of the user 110 and select plans with the highest predictor value (e.g., 90% match over 30% match, etc.) for selection for presentation in a user interface. For example the available plan options may be presented to the user 110 in descending order of the prediction value indicating the plans in an order that they are predicted to match the attributes of the user 110. In an example, the user 110 may be presented with a preferences user interface that allows the user to input preferences for plan options. For example, the user interface may include interactive elements that enable the user 110 to rank plan attributes based on importance to the user 110, select important attributes, select a goal (e.g., limit cost, maximize benefits, etc.), select plan benefits important to the user 110, etc.

The systems and techniques discussed herein provide an improved GAN model that is able to provide granular data evaluation while maintain privacy and data privacy compliance to improve the ability for the artificial intelligence model to predict plans for organizations and employees. Computing resource utilization may be reduced by providing a variety of recommendations individually tailored to the organization and the user in parallel preventing repetitive prediction calculations for individual plans. These technical features enable quicker and less complicated insurance decision making based on an analysis that is often hard or time-consuming for organizations and employees to reproduce or locate.

It will be understood that the systems and techniques discussed herein are applicable to a wide variety of business from small businesses to large conglomerate organizations.

Figure 2:
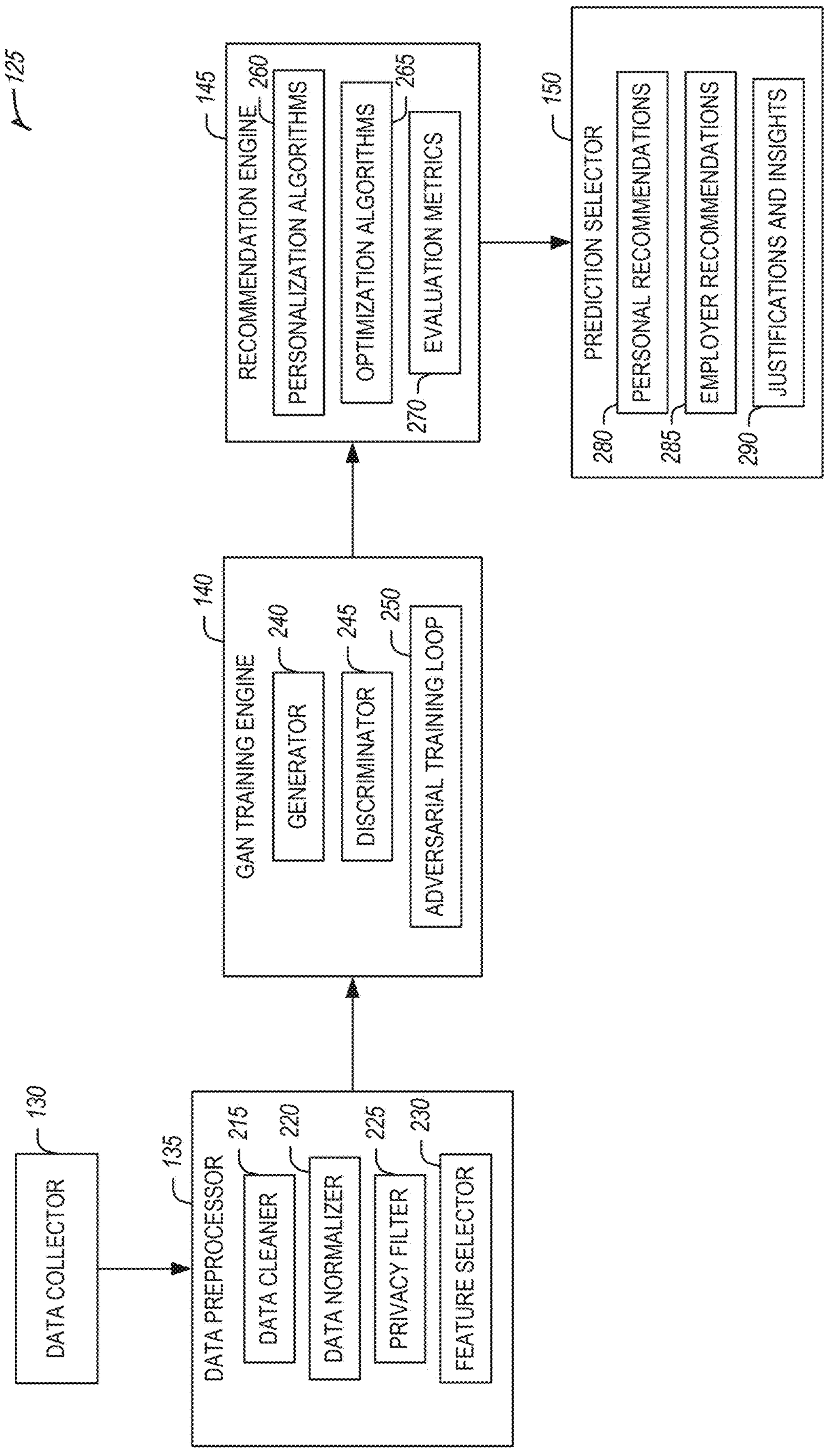
FIG. 2 illustrates an example of a system for a, according to an embodiment.

FIG. 2 illustrates a more detailed example of the system 125, according to an embodiment. The data collector 130 may obtain the data from the profile database 115. Data may include, by way of example and not limitation, business profiles, employee demographics, health spending history, regulatory requirements, feedback and ratings, healthcare usage (e.g., number of doctor visits, virtual visits, vaccination records, etc.), demographics, chronic condition information, etc. The user 110 may opt in to provide more detailed data. For example, the user 110 may grant access to explanation of benefits documents, heath spending account data, flexible spending account data, diagnostic test results, demographical data, financial account data, and the like. Rewards may be offered for providing data or opting in such as, by way of example and not limitation, a premium discount, a contribution to a health savings account, etc. The organization 105 may provide data manually or automatically including, by way of example and not limitation, organization type, previous insurer, revenue, number of employees, organizational structure, healthcare spending, current healthcare premiums, and the like. In an example, the organization 105 and/or the user 110 may be presented with a user interface that includes a questionnaire that request data that may be helpful in providing customized recommendations. The data input into the user interface may be added to the profile database 115.

The data preprocessor 135 cleans, normalizes, and transforms the collected data to ensure it is suitable for training AI models and applies privacy filters to protect sensitive information. The data preprocessor 135 may include a number of components including a data cleaner 215, a data normalizer 220, a privacy filter 225, and a feature selector 230. The data cleaner 215 may aggregate, trim, and remove noisy elements from the data. The data normalizer 220 may reformat, convert, or otherwise modify the data as appropriate for feature extraction. The privacy filter 225 may anonymize and remove confidential data elements from the data. The feature selector 230 identifies and selects features from the data to be used in training AI models to make predictions and to evaluate using the AL models to generate a prediction.

Generative Adversarial Networks (GANs) are a class of artificial intelligence models used in unsupervised machine learning. They consist of two neural networks, the generator and the discriminator, which are trained simultaneously through adversarial processes. The GAN training engine 140 includes a generator 240, a discriminator 245, and an adversarial training loop 250. The GAN training engine 140 uses features extracted from historical info from other organizations and similarly situated individuals that selected and did not select a plan based on multiple categories (e.g., with similar healthcare spending, social ability, medical conditions, employer size, etc.). In an example, an algorithm may be created for a demographic such as a chronic condition and recommendation predictions may be adjusted or weighted.

The generator 240 creates synthetic profiles of organizations and employees based on input features such as demographics, health spending history, and other relevant attributes. The synthetic profiles are designed to mimic real-world data without using actual sensitive information, thus preserving privacy.

The discriminator 245 is trained on real-world data, including actual healthcare plan selections, outcomes, and feedback from organizations and employees. Its role is to distinguish between the synthetic profiles created by the generator 240 and the real profiles.

During training, in the adversarial training loop 250, the generator 240 tries to produce increasingly realistic profiles that can 'fool' the discriminator 255 into thinking they are real. Conversely, the discriminator 255 learns to get better at distinguishing real data from the fake data produced by the generator 250. This adversarial process continues until the generator 250 produces profiles that are indistinguishable from real ones to the discriminator 255.

Once trained, the generator 250 is used to create a large dataset of synthetic profiles that reflect a wide range of possible organization and employee scenarios. This dataset is used to explore and understand the space of healthcare plan needs without compromising individual privacy.

The recommendation engine 145 includes personalization algorithms 260, optimization algorithms 265, and evaluation metrics 270. The personalization algorithms 260 uses the trained generator 250 to simulate how different profiles would react to various healthcare plans. This component uses the models from the GAN training engine 140 along with the personalization algorithms 260 and the optimization algorithms 265 to generate healthcare plan recommendations. It evaluates plans using the evaluation metrics 270 to ensure they meet the needs of the business and employees. By analyzing the synthetic data, patterns and preferences are learned that are common to certain types of organizations and employee groups. The role of the discriminator 245 in the recommendation engine 145 is to evaluate the quality of the recommendations made by the generator. The optimization algorithms 265 assess whether the suggested plans are realistic and beneficial for the synthetic profiles. This feedback loop allows the GAN training engine 140 to refine its recommendation models.

The prediction selector 150 generates personal recommendations 280 for employees and employer recommendations 285 for organizations. The final output of the system 125, where personalized healthcare plan suggestions are provided to the users along with justifications and insights to aid in decision-making. For individual employees or businesses that opt-in, personalize recommendations are created by generating a set of potential healthcare plans and predicting their suitability based on the specific characteristics of the business or employee profile. Justifications and insights 290 are generated and included in the recommendations to prove an organization or user with considerations of the recommendations.

As the GAN training engine 140 receives more real-world data and feedback, the GAN training engine 140 retrains its networks (models) to improve its accuracy and adapt to changes in healthcare regulations, market conditions, and user preferences. The GAN training engine 140 generates highly personalized, adaptable, and privacy-preserving healthcare plan recommendations, in conjunction with the recommendation engine 145 and the prediction selector 150, for organizations and their employees. The GAN training engine 140 continuously improves its recommendations as it processes more data, ensuring that it remains up-to-date with the latest trends and regulations in healthcare.

Figure 3:
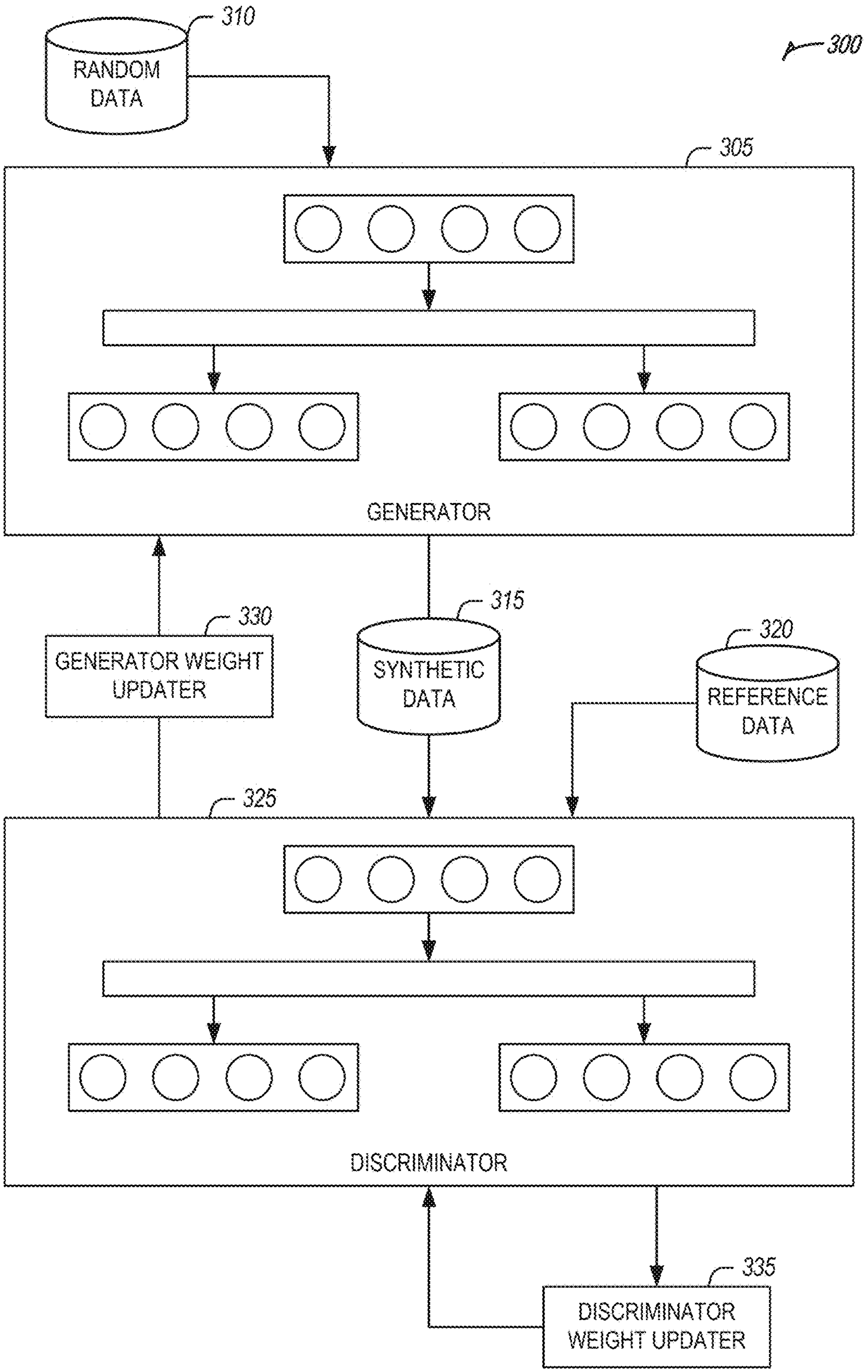
FIG. 3 illustrates an example of a data flow for a, according to an embodiment.

FIG. 3 illustrates an example of a data flow for a, according to an embodiment. Random data 310 is input into the generator 305. The generator 305 creates synthetic data 315 that mimics the characteristics of the collected data without using actual sensitive information. The discriminator 325 analyzes both reference data 320 and the synthetic data 315 to distinguish between them. An iterative process is employed where the generator and discriminator improve through competition. The results of the iterative process are used by a discriminator weight updater 335 to retrain the network of the discriminator 325 and by a generator weight updater 330 to retrain the network of the generator 305.

Figure 4:
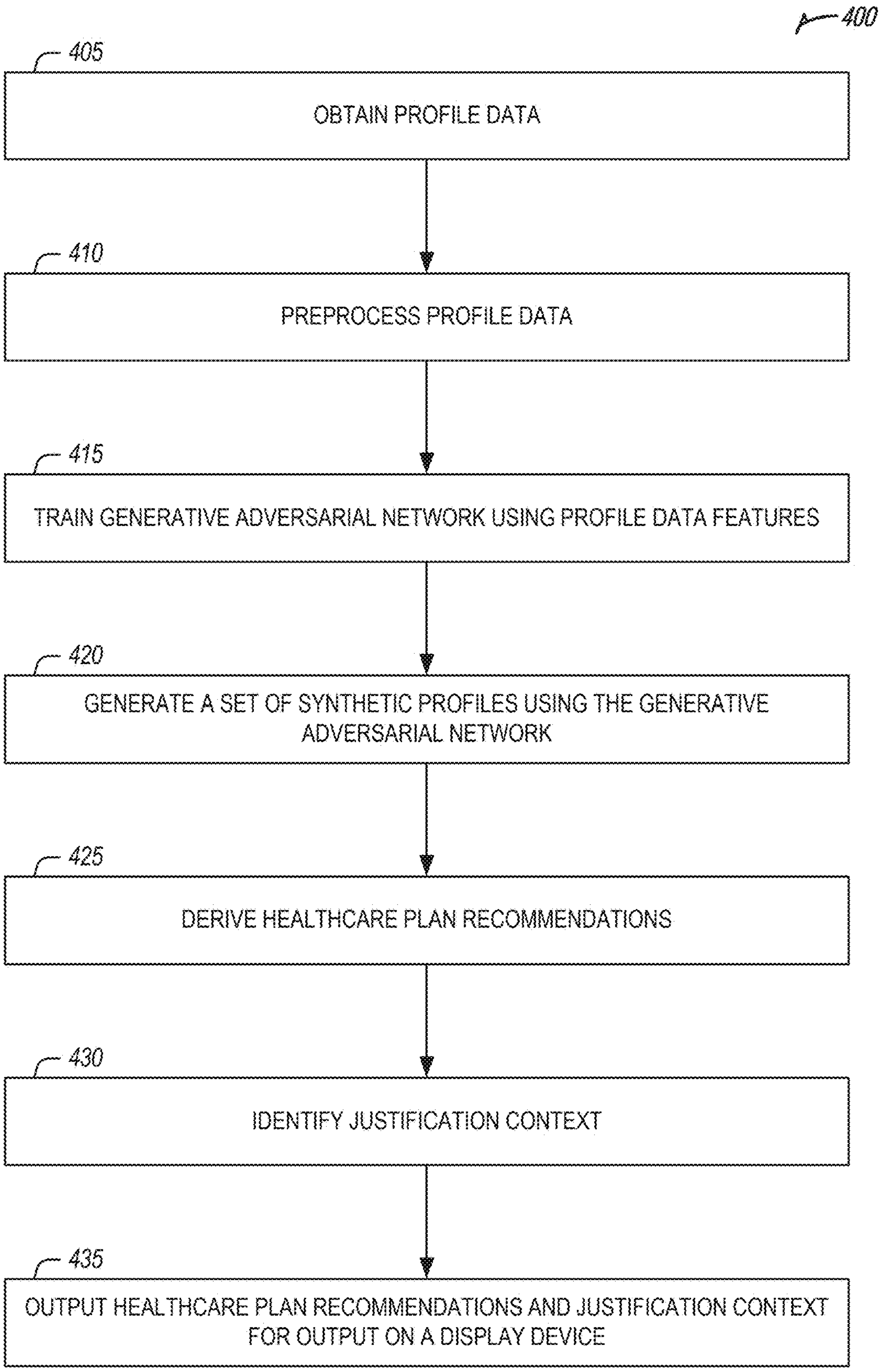
FIG. 4 illustrates an example of a method for, according to an embodiment.

FIG. 4 illustrates an example of a method 400 for, according to an embodiment. The method 400 may provide features as described in FIGS. 1 to 3.

Profile data is obtained (e.g., by the data collector as described in FIG. 1, etc.) for a user and an organization (e.g., at operation 405). In an example, the profile data may include one or more data elements comprising healthcare spending data, demographic data, health condition data, and organizational data.

The profile data is preprocessed (e.g., by the data processor 135 as described in FIG. 1, etc.) to generate a normalized data set (e.g., at operation 410). In an example, a sensitive data element may be identified in the profile data and anonymization may be applied to the sensitive data element.

A generative adversarial network is trained (e.g., by the GAN training engine 140 as described in FIG. 1, etc.) using features extracted from the normalized data set (e.g., at operation 415). In an example, a generator network may be trained to generate synthetic profiles and a discriminator network may be trained to distinguish between the synthetic profiles and real profiles. In an example, an adversarial training loop may be performed until the discriminator fails to distinguish between the synthetic profiles and the real profiles.

A set of synthetic profiles are generated (e.g., by the generator 240 as described in FIG. 2, etc.) using the generative adversarial network (e.g., at operation 420). A set of healthcare plan recommendations are derived (e.g., by the recommendation engine 145 as described in FIG. 1, etc.) using the set of synthetic profiles (e.g., at operation 425).

Justification context is determined (e.g., by the prediction selector 150 as described in FIG. 1, etc.) for each healthcare plan recommendation (e.g., at operation 430). In an example, the discriminator network may be trained to generate a context map for a healthcare plan recommendation of the set of healthcare recommendations. The context map may include data elements and rules used in calculating a probability of a match between the profile data and a healthcare plan associated with the healthcare plan recommendation. The justification context for the healthcare plan recommendation may be generated using the context map.

An interactive healthcare plan recommendation user interface is generated (e.g., by the prediction selector 150 as described in FIG. 1, etc.), for output on a display device, comprising the set of healthcare plan recommendations and the justification context (e.g., at operation 435). In an example, feedback regarding the set of healthcare plan recommendations may be obtained and the discriminator network may be retrained using the feedback.

Figure 5:
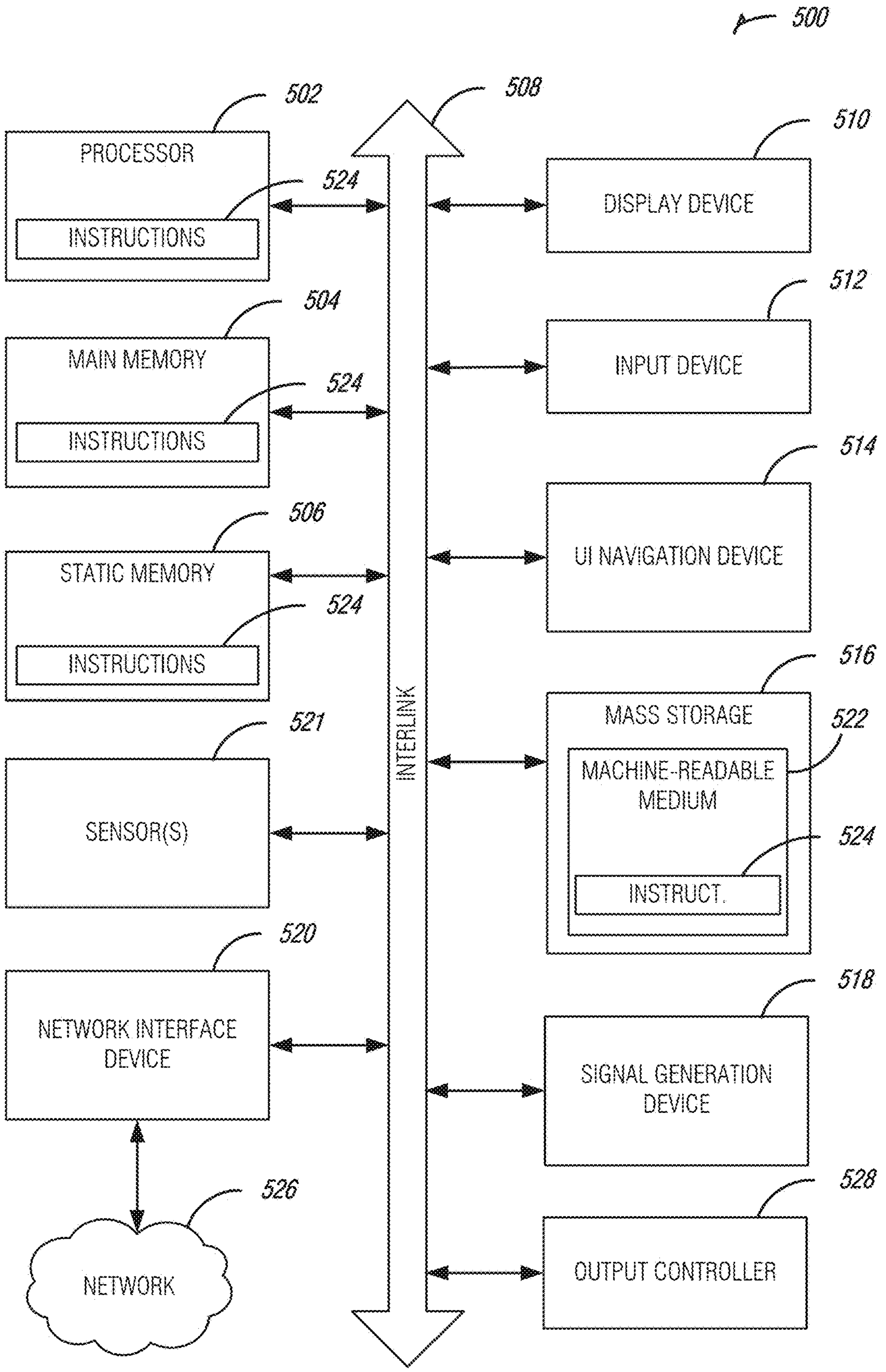
FIG. 5 is a block diagram illustrating an example of a machine upon which one or more embodiments may be implemented.

FIG. 5 illustrates a block diagram of an example machine 500 upon which any one or more of the techniques (e.g., methodologies) discussed herein may perform. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensors. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media. In an example, machine readable media may exclude transitory propagating signals (e.g., non-transitory machine-readable storage media). Specific examples of non-transitory machine-readable storage media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, LoRa®/LoRaWAN® LPWAN standards, etc.), IEEE 802.15.4 family of standards, peer-to-peer (P2P) networks, 3$^{rd}$ Generation Partnership Project (3GPP) standards for 4G and 5G wireless communication including: 3GPP Long-Term evolution (LTE) family of standards, 3GPP LTE Advanced family of standards, 3GPP LTE Advanced Pro family of standards, 3GPP New Radio (NR) family of standards, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

Additional Notes

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A system for a generative adversarial network recommendation engine, comprising:

at least one processor; and memory comprising instructions that, when executed by the at least one processor, cause the at least one processor to perform operations to:

obtain profile data for a user and an organization;

preprocess the profile data to generate a normalized data set by applying anonymization to sensitive data elements in the profile data, and normalizing values across the profile data;

train a generative adversarial network using features extracted from the normalized data set including operations to:

train a generator network to generate synthetic profiles; and train a discriminator network to distinguish between the synthetic profiles and real profiles including training the discriminator network on real-world data including actual healthcare plan selections, outcomes, and feedback from organizations and employees to distinguish between the synthetic profiles and real profiles, wherein the trained discriminator network evaluates whether suggested healthcare plans are realistic and beneficial for the synthetic profiles;

generate a set of synthetic profiles using the generative adversarial network;

calculate risk scores for the set of synthetic profiles based on health and demographic characteristics represented in the synthetic profiles;

derive a first set of healthcare plan recommendations using the set of synthetic profiles for the organization using aggregate risk scores and aggregate characteristics from the set of synthetic profiles;

derive a second set of healthcare plan recommendations for the user using individual risk scores and individual characteristics from the set of synthetic profiles;

determine justification context for each healthcare plan recommendation;

generate an interactive healthcare plan recommendation user interface, for output on a display device, comprising the first set of healthcare plan recommendations for the organization with corresponding aggregate risk assessments, the second set of healthcare plan recommendations for the user with corresponding individual risk assessments, and the justification context for each recommendation;

generate a context map for a healthcare plan recommendation of the set of healthcare recommendations;

generate the justification context for the healthcare plan recommendation using the context map, the justification context including at least one of considerations of the recommendations, pros and cons, or explanations of user or organization attributes used to make a prediction;

obtain feedback regarding the set of healthcare plan recommendations as an updated feedback dataset, wherein the feedback comprises at least one of user ratings, review information, or subscriber interaction data; and retrain the discriminator network using the updated feedback dataset by:

providing the updated feedback dataset as training data to the discriminator network;

adjusting network parameters of the discriminator network through an adversarial training process where the discriminator network learns to better distinguish between synthetic profiles and real profiles based on the updated feedback dataset; and iteratively updating weights of the discriminator network until convergence criteria are met to improve accuracy of the discriminator network in evaluating healthcare plan recommendations.

2. The system of claim 1, wherein the profile data includes one or more data elements comprising healthcare spending data, demographic data, health condition data, and organizational data.

3. The system of claim 1, the instructions to preprocess the profile data further comprising instructions that, when executed by the at least one processor, cause the at least one processor to perform operations to:

identify a sensitive data element in the profile data; and apply anonymization to the sensitive data element.

4. The system of claim 1, the instructions to train the discriminator network further comprising instructions that, when executed by the at least one processor, cause the at least one processor to perform operations to perform an adversarial training loop until the discriminator fails to distinguish between the synthetic profiles and the real profiles.

5. The system of claim 1, the instructions to train the generative adversarial network further comprising instructions that, when executed by the at least one processor, cause the at least one processor to perform operations to:

train the discriminator network on real-world data including actual healthcare plan selections, outcomes, and feedback from organizations and employees to distinguish between the synthetic profiles and real profiles, wherein the trained discriminator network evaluates whether suggested healthcare plans are realistic and beneficial for the synthetic profiles;

generate the context map further comprising instructions that, when executed by the at least one processor, cause the at least one processor to perform operations of: for a healthcare plan recommendation of the set of healthcare recommendations by:

analyzing the synthetic data to identify patterns and preferences common to types of organizations and employee groups;

determining data elements including at least one of co-pay information, network providers, deductible information, and plan features; and applying rules for calculating a probability of a match between the profile data and a healthcare plan associated with the healthcare plan recommendation based on the identified patterns; and generate the justification context for the healthcare plan recommendation using the context map, wherein the justification context includes at least one of considerations of the recommendations, pros and cons, or explanations of user or organization attributes used to make a prediction.

6. At least one non-transitory machine-readable medium including instructions for a generative adversarial network recommendation engine that, when executed by at least one processor, cause the at least one processor to perform operations to:

obtain profile data for a user and an organization;

preprocess the profile data to generate a normalized data set by applying anonymization to sensitive data elements in the profile data, and normalizing values across the profile data;

train a generative adversarial network using features extracted from the normalized data set including operations to:

train a generator network to generate synthetic profiles; and train a discriminator network to distinguish between the synthetic profiles and real profiles including training the discriminator network on real-world data including actual healthcare plan selections, outcomes, and feedback from organizations and employees to distinguish between the synthetic profiles and real profiles, wherein the trained discriminator network evaluates whether suggested healthcare plans are realistic and beneficial for the synthetic profiles;

generate a set of synthetic profiles using the generative adversarial network;

calculate risk scores for the set of synthetic profiles based on health and demographic characteristics represented in the synthetic profiles;

derive a first set of healthcare plan recommendations using the set of synthetic profiles for the organization using aggregate risk scores and aggregate characteristics from the set of synthetic profiles;

derive a second set of healthcare plan recommendations for the user using individual risk scores and individual characteristics from the set of synthetic profiles;

determine justification context for each healthcare plan recommendation;

generate an interactive healthcare plan recommendation user interface, for output on a display device, comprising the first set of healthcare plan recommendations for the organization with corresponding aggregate risk assessments, the second set of healthcare plan recommendations for the user with corresponding individual risk assessments, and the justification context for each recommendation;

generate a context map for a healthcare plan recommendation of the set of healthcare recommendations;

generate the justification context for the healthcare plan recommendation using the context map, the justification context including at least one of considerations of the recommendations, pros and cons, or explanations of user or organization attributes used to make a prediction;

obtain feedback regarding the set of healthcare plan recommendations as an updated feedback dataset, wherein the feedback comprises at least one of user ratings, review information, or subscriber interaction data; and retrain the discriminator network using the updated feedback dataset by:

providing the updated feedback dataset as training data to the discriminator network;

adjusting network parameters of the discriminator network through an adversarial training process where the discriminator network learns to better distinguish between synthetic profiles and real profiles based on the updated feedback dataset; and iteratively updating weights of the discriminator network until convergence criteria are met to improve accuracy of the discriminator network in evaluating healthcare plan recommendations.

7. The at least one non-transitory machine-readable medium of claim 6, wherein the profile data includes one or more data elements comprising healthcare spending data, demographic data, health condition data, and organizational data.

8. The at least one non-transitory machine-readable medium of claim 6, the instructions to preprocess the profile data further comprising instructions that, when executed by the at least one processor, cause the at least one processor to perform operations to:

identify a sensitive data element in the profile data; and apply anonymization to the sensitive data element.

9. The at least one non-transitory machine-readable medium of claim 6, the instructions to train the discriminator network further comprising instructions that, when executed by the at least one processor, cause the at least one processor to perform operations to perform an adversarial training loop until the discriminator fails to distinguish between the synthetic profiles and the real profiles.

10. The at least one non-transitory machine-readable medium of claim 6, the instructions to train the generative adversarial network further comprising instructions that, when executed by the at least one processor, cause the at least one processor to perform operations to:

train the discriminator network on real-world data including actual healthcare plan selections, outcomes, and feedback from organizations and employees to distinguish between the synthetic profiles and real profiles, wherein the trained discriminator network evaluates whether suggested healthcare plans are realistic and beneficial for the synthetic profiles;

generate the context map further comprising instructions that, when executed by the at least one processor, cause the at least one processor to perform operations of: for a healthcare plan recommendation of the set of healthcare recommendations by:

analyzing the synthetic data to identify patterns and preferences common to types of organizations and employee groups;

determining data elements including at least one of co-pay information, network providers, deductible information, and plan features; and applying rules for calculating a probability of a match between the profile data and a healthcare plan associated with the healthcare plan recommendation based on the identified patterns; and generate the justification context for the healthcare plan recommendation using the context map, wherein the justification context includes at least one of considerations of the recommendations, pros and cons, or explanations of user or organization attributes used to make a prediction.

11. A method for a generative adversarial network recommendation engine, comprising:

obtaining profile data for a user and an organization;

preprocessing the profile data to generate a normalized data set by applying anonymization to sensitive data elements in the profile data, and normalizing values across the profile data;

training a generative adversarial network using features extracted from the normalized data set including operations to:

train a generator network to generate synthetic profiles; and train a discriminator network to distinguish between the synthetic profiles and real profiles including training the discriminator network on real-world data including actual healthcare plan selections, outcomes, and feedback from organizations and employees to distinguish between the synthetic profiles and real profiles, wherein the trained discriminator network evaluates whether suggested healthcare plans are realistic and beneficial for the synthetic profiles;

generating a set of synthetic profiles using the generative adversarial network;

calculating risk scores for the set of synthetic profiles based on health and demographic characteristics represented in the synthetic profiles;

deriving a first set of healthcare plan recommendations using the set of synthetic profiles for the organization using aggregate risk scores and aggregate characteristics from the set of synthetic profiles;

deriving a second set of healthcare plan recommendations for the user using individual risk scores and individual characteristics from the set of synthetic profiles;

determining justification context for each healthcare plan recommendation;

generating an interactive healthcare plan recommendation user interface, for output on a display device, comprising the first set of healthcare plan recommendations for the organization with corresponding aggregate risk assessments, the second set of healthcare plan recommendations for the user with corresponding individual risk assessments, and the justification context for each recommendation;

generate a context map for a healthcare plan recommendation of the set of healthcare recommendations;

generate the justification context for the healthcare plan recommendation using the context map, the justification context including at least one of considerations of the recommendations, pros and cons, or explanations of user or organization attributes used to make a prediction;

obtain feedback regarding the set of healthcare plan recommendations as an updated feedback dataset, wherein the feedback comprises at least one of user ratings, review information, or subscriber interaction data; and retrain the discriminator network using the updated feedback dataset by:

providing the updated feedback dataset as training data to the discriminator network;

adjusting network parameters of the discriminator network through an adversarial training process where the discriminator network learns to better distinguish between synthetic profiles and real profiles based on the updated feedback dataset; and iteratively updating weights of the discriminator network until convergence criteria are met to improve accuracy of the discriminator network in evaluating healthcare plan recommendations.

12. The method of claim 11, wherein preprocessing the profile data further comprises:

identifying a sensitive data element in the profile data; and applying anonymization to the sensitive data element.

13. The method of claim 11, wherein training the discriminator network further comprises performing an adversarial training loop until the discriminator fails to distinguish between the synthetic profiles and the real profiles.

14. The method of claim 11, wherein training the generative adversarial network further comprises:

training the discriminator network on real-world data including actual healthcare plan selections, outcomes, and feedback from organizations and employees to distinguish between the synthetic profiles and real profiles, wherein the trained discriminator network evaluates whether suggested healthcare plans are realistic and beneficial for the synthetic profiles;

generating the context map includes: for a healthcare plan recommendation of the set of healthcare recommendations by:

analyzing the synthetic data to identify patterns and preferences common to types of organizations and employee groups;

determining data elements including at least one of co-pay information, network providers, deductible information, and plan features; and applying rules for calculating a probability of a match between the profile data and a healthcare plan associated with the healthcare plan recommendation based on the identified patterns; and generating the justification context for the healthcare plan recommendation using the context map, wherein the justification context includes at least one of considerations of the recommendations, pros and cons, or explanations of user or organization attributes used to make a prediction.

* * * * *